US012740853B2

(12) United States Patent
Heo et al.

(10) Patent No.: US 12,740,853 B2
(45) Date of Patent: Sep. 22, 2026

(54) ARTIFICIAL PROSTHESIS AND METHOD FOR MANUFACTURING SAME

(71) Applicant: Seoul National University Hospital, Seoul (KR)

(72) Inventors: Chan Yeong Heo, Gyeonggi-do (KR); Sun-Young Nam, Gyeonggi-do (KR); Byung-Ho Shin, Gyeonggi-do (KR)

(73) Assignee: Seoul National University Hospital, Seoul (KR)

( * ) Notice: Subject to any disclaimer, the term of this patent is extended or adjusted under 35 U.S.C. 154(b) by 1218 days.

(21) Appl. No.: 17/761,483

(22) PCT Filed: Sep. 24, 2020

(86) PCT No.: PCT/KR2020/012989

§ 371 (c)(1),
(2) Date: Oct. 7, 2022

(87) PCT Pub. No.: WO2021/060883

PCT Pub. Date: Apr. 1, 2021

(65) Prior Publication Data

US 2023/0061211 A1 Mar. 2, 2023

(30) Foreign Application Priority Data

Sep. 24, 2019 (KR) ........................ 10-2019-0117430

(51) Int. Cl.
*A61F 2/12* (2006.01)
*A61F 2/00* (2006.01)

(52) U.S. Cl.
CPC .............. *A61F 2/12* (2013.01); *A61F 2/0077* (2013.01); *A61F 2002/0081* (2013.01)

(58) Field of Classification Search
CPC ....... A61F 2/12; A61F 2/0077; A61L 2430/04
See application file for complete search history.

(56) References Cited

U.S. PATENT DOCUMENTS

| | | | | |
|---|---|---|---|---|
| 4,955,909 | A | 9/1990 | Ersek et al. | |
| 5,207,709 | A * | 5/1993 | Picha | A61L 27/18 623/8 |
| 6,319,264 | B1 * | 11/2001 | Tormala | D04B 21/12 606/151 |
| 2003/0204270 | A1 * | 10/2003 | Berman | A61L 17/04 623/23.72 |

(Continued)

FOREIGN PATENT DOCUMENTS

| | | | |
|---|---|---|---|
| JP | 2016533244 | A | 10/2016 |
| KR | 1020110055129 | A | 5/2011 |

(Continued)

OTHER PUBLICATIONS

International Search Report for International Application No. PCT/KR2020/012989, dated Jan. 7, 2021, 5 pages.

*Primary Examiner* — Bruce E Snow
(74) *Attorney, Agent, or Firm* — McNeill PLLC

(57) ABSTRACT

Disclosed are an artificial prosthesis and a method for manufacturing same. The artificial prosthesis includes a surface having a pattern formed thereon, the pattern comprising straight line shapes aligned in parallel with each other, and has the effect of reducing inflammation in a region implanted with the prosthesis, and effectively reducing capsular contracture side effects.

9 Claims, 8 Drawing Sheets

(56) References Cited

U.S. PATENT DOCUMENTS

| | | | | |
|---|---|---|---|---|
| 2009/0093879 | A1* | 4/2009 | Wawro | A61F 2/0077 623/11.11 |
| 2009/0255618 | A1 | 10/2009 | Tassone et al. | |
| 2012/0245685 | A1 | 9/2012 | Yu | |
| 2023/0061211 | A1* | 3/2023 | Heo | A61F 2/12 |

FOREIGN PATENT DOCUMENTS

| | | | |
|---|---|---|---|
| KR | 1020180107578 | A | 10/2018 |
| WO | 2009046425 | A2 | 4/2009 |
| WO | 2009126507 | A2 | 10/2009 |
| WO | 2015040106 | A1 | 3/2015 |
| WO | 2018188930 | A1 | 10/2018 |

* cited by examiner

ARTIFICIAL PROSTHESIS AND METHOD FOR MANUFACTURING SAME

TECHNICAL FIELD

The present disclosure is related to an artificial prosthesis and a method for manufacturing the same.

[the National R&D Projects Supporting the Invention]
[Project ID number] HI15C1744
[Government department name] The Ministry of Health-Welfare
[Research management institution] Korea Health Industry Development Institute
[Research business title] Technical development of medical devices
[Research project title] Development of implantable silicone prosthesis with fiberization inhibition
[Contribution ratio] 1/1
[Management department] Seoul National University Bundang Hospital
[Research period] Nov. 1, 2015 to Oct. 31, 2020

BACKGROUND ART

Silicone prostheses are medical devices commonly used in plastic and reconstructive surgical procedures. As there is a growing interest in the plastic surgery, surgeries to implement silicone prostheses, particularly breast augmentation, is increasing. However, silicon implantation may cause foreign body response (FBR) for the human body to remove foreign bodies from an immune system. As a result of this essential reaction, the main side effect caused by a silicone prosthesis is the capillary contracture.

A foreign body response isolates a silicone prosthesis by a long-term inflammatory reaction and thus forms excessive fibrous capsules composed of collagen and fibroblasts around the prosthesis. Collagen and fibroblasts further compress capsules and contract a prosthesis, and thus result in a hard and deformed prosthesis that causes severe pain and discomfort and may require re-surgeries to treat side effects in severe cases.

Macrophages are a major cause of excessive inflammatory responses, and are also one of the major cell types that appear around a prosthesis site within 48-72 hours after implantation.

These cells provide an initial immune response, remove foreign pathogens through phagocytosis, collect other immune cells for further defense, and activate complement and adaptive immune systems. Macrophages may be polarized into various phenotypes (M1 and M2a-c) on the basis of the environment thereof, including chemical, physical, and temporal properties.

Immediately after implantation, a foreign body reaction is initiated, and non-specific proteins from serum are adsorbed on a prosthesis surface. These proteins form blood clots that include chemoattractants, cytokines, and growth factors that send immune cells to an implantation site. Macrophages along with platelets and monocytes penetrate and adhere to a prosthesis after a few hours or days and are polarized to a pro-inflammatory (M1) phenotype. M1 macrophages secrete pro-inflammatory cytokines and chemokines (TNF-$\alpha$, IL-6, IL-1$\beta$, and MIP-1), and send signals to collect other immune cells to a prosthesis site. When several weeks pass, macrophages begin to polarize into a selectively activated pre-healing (M2) phenotype. M2 macrophages secrete cytokines IL-4, IL-10, IL-13, and TGF-$\beta$ to induce a healing mechanism. Furthermore, M1 cells have a round shape while M2 cells are characterized by longer elongation. As such, a foreign body response results in fibrous encapsulation of a prosthesis due to fibroblast gathering, collagen deposition and fusion of maximum 100 macrophages.

DISCLOSURE

Technical Problem

In an aspect, an object of the present disclosure is to provide an artificial prosthesis that reduces inflammation at an implantation site and effectively reduces capsular contracture side effects.

In another aspect, an object of the present disclosure is to provide a method for manufacturing the artificial prosthesis.

Solution to Problem

In an aspect, a technology disclosed herein provides an artificial prosthesis including a surface having a pattern formed thereon, the pattern having a straight shape and being aligned in parallel.

In an example embodiment, the pattern may be formed by alternate repeated parallel alignment of straight embossed portions and engraved portions.

In an example embodiment, the embossed portions may be aligned at intervals of 5 to 35 μm, and/or the engraved portions may be aligned at intervals of 5 to 35 μm.

In an example embodiment, the width of the embossed portions and the width of the engraved portion may have the same length, or the width of the embossed portions may be greater than the width of the engraved portions.

In an example embodiment, the width of the embossed portions may be 1 to 5 μm greater than the width of the engraved portions.

In an example embodiment, a height difference between the highest point of the embossed portions and the lowest point of the engraved portions may be 0.01 to 1.5 mm.

In an example embodiment, the prosthesis may be formed of silicone.

In an example embodiment, the prosthesis may be a breast prosthesis.

In an example embodiment, the prosthesis may be for inhibiting capsular contracture.

In an example embodiment, the prosthesis may be for inhibiting an inflammatory response.

In another aspect, a technology disclosed herein provides a method of manufacturing an artificial prosthesis, the method including forming a pattern on the surface thereof, the pattern having a straight shape and being aligned in parallel.

In an example embodiment, the method may include: manufacturing a substrate having a straight and parallel aligned pattern; and injecting silicone into the substrate and hardening the silicone.

In an example embodiment, the pattern may be formed by alternate repeated parallel alignment of straight embossed portions and engraved portions.

In an example embodiment, the embossed portions may be aligned at intervals of 5 to 35 μm, and/or the engraved portions may be aligned at intervals of 5 to 35 μm.

In an example embodiment, the width of the embossed portions and the width of the engraved portion may have the same length, or the width of the embossed portions may be greater than the width of the engraved portions.

In an example embodiment, the width of the embossed portions may be 1 to 5 μm greater than the width of the engraved portions.

In an example embodiment, a height difference between the highest point of the embossed portions and the lowest point of the engraved portions may be 0.01 to 1.5 mm.

Advantageous Effects of the Invention

In an aspect, the techniques disclosed herein have the effect of providing an artificial prosthesis that reduces inflammation at an implantation site and effectively reduces capsular contracture side effects.

In another aspect, the techniques disclosed herein have the effect of providing a method for manufacturing the artificial prosthesis.

BRIEF DESCRIPTION OF DRAWINGS

FIG. 6B is a graph comparing the thickness of a hard and dense capsule formed on a portion contacting the silicon prosthesis shown by the blue arrow in FIG. 6A.

MODE FOR INVENTION

Figure 1:
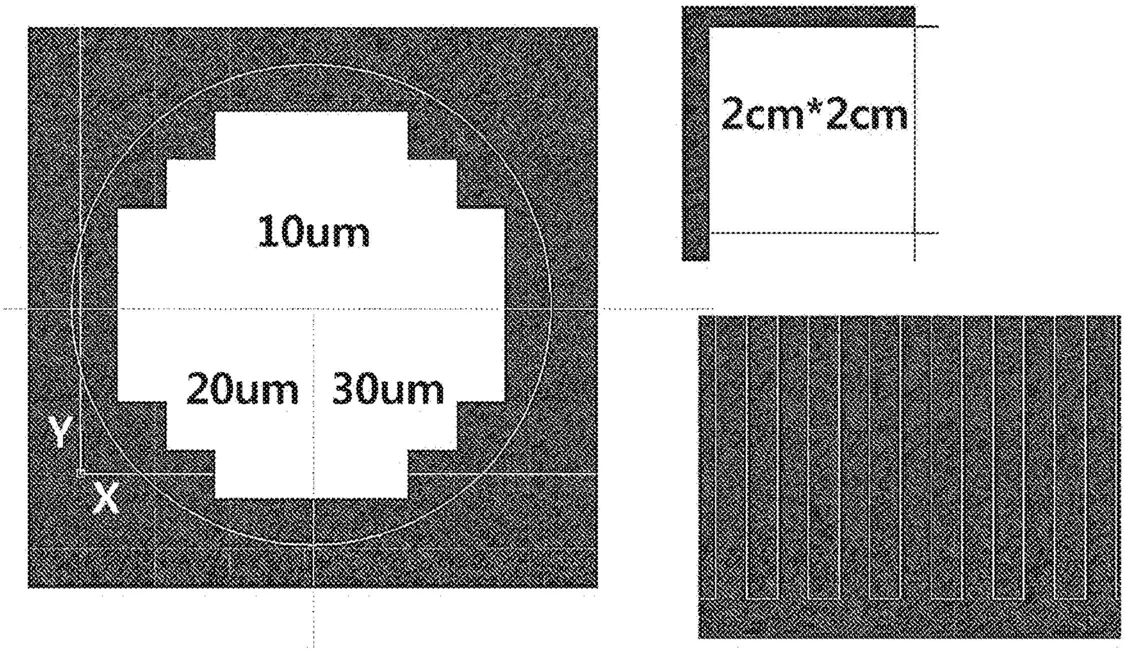
FIG. 1 illustrates a schematic view of a patterned substrate design according to an example of the present disclosure.

Hereinafter, the present disclosure will be described in detail.

In an aspect, a technology disclosed herein provides an artificial prosthesis including a surface having a pattern formed thereon, the pattern having a straight shape and being aligned in parallel.

In the present disclosure, an "aligned pattern" refers to a pattern in which straight patterns extending in one direction are arranged in parallel at regular intervals.

In an example embodiment, the pattern may be formed by alternate repeated parallel alignment of straight embossed portions and engraved portions.

In an example embodiment, the embossed portions may be aligned at intervals of 5 to 35 μm, and/or the engraved portions may be aligned at intervals of 5 to 35 μm.

In an example embodiment, the width of the embossed portions and/or the width of the engraved portions may be 5 to 35 μm. The "width of the embossed portions" may refer to a length between an engraved portion and another engraved portion (e.g. the length of a in FIG. 2), and the "width of the engraved portions" may refer to a length between an embossed portion and another embossed portion (e.g. the length of b in FIG. 2).

In another example embodiment, the width of the embossed portions and/or the width of the engraved portions may be 5 μm or more, 6 μm or more, 7 μm or more, 8 μm or more, 9 μm or more, 10 μm or more, 11 μm or more, 12 μm or more, 13 μm or more, 14 μm or more, 15 μm or more, 16 μm or more, 17 μm or more, 18 (or more, 19 μm or more, or 20 μm or more, and 35 μm or less, 34 μm or less, 33 μm or less, 32 μm or less, 31 μm or less, 30 μm or less, 29 μm or less, 28 μm or less, 27 μm or less, 26 μm or less, 25 μm or less, 24 μm or less, 23 μm or less, 22 μm or less, 21 μm or less, or 20 μm or less.

In an example embodiment, the width of the embossed portions may be 20 to 30 μm.

In an example embodiment, the width of the engraved portions may be 10 to 30 μm.

In an example embodiment, it may be preferred that in the prosthesis, the width of the embossed portions is 20 to 30 μm and the width of the engraved portions is 10 to 30 μm.

In an example embodiment, the width of the embossed portions and the width of the engraved portion may have the same length, or the width of the embossed portions may be greater than the width of the engraved portions.

In an example embodiment, the width of the embossed portions may be greater than the width of the engraved portions by 1 to 5 μm.

In another example embodiment, the width of the embossed portions may be greater than the width of the engraved portions by at least 1 μm or more, 2 μm or more, 3 μm or more, 4 μm or more, and 5 μm or less, 4 μm or less, 3 μm or less, or 2 μm or less.

In an example embodiment, a height difference between the highest point of the embossed portions and the lowest point of the engraved portions may be 0.01 to 1.5 mm. The "highest point" and the "lowest point" may refer to the highest point and the lowest point on the height.

In another example embodiment, a height difference between the highest point of the embossed portions and the lowest point of the engraved portions may be 0.01 mm or more, 0.02 mm or more, 0.03 mm or more, 0.04 mm or more, 0.05 mm or more, 0.06 mm or more, 0.07 mm or more, 0.08 mm or more, 0.09 mm or more, 0.1 mm or more, 0.2 mm or more, 0.3 mm or more, 0.4 mm or more, or 0.5 mm or more, and 1.5 mm or less, 1.4 mm or less, 1.3 mm or less, 1.2 mm or less, 1.1 mm or less, 1.0 mm or less, 0.9 mm or less, 0.8 mm or less, 0.7 mm or less, 0.6 mm or less, 0.5 mm or less, 0.4 mm or less, 0.3 mm or less, 0.2 mm or less, or 0.1 mm or less.

The artificial prosthesis according to the present disclosure includes a surface on which the same patterns are formed at regular intervals as described above, and thus it is possible to upregulate the polarization of macrophages into M2 phenotypes, thereby reducing inflammation at an implantation site, promoting tissue restoration, reducing the side effects of capsular contracture.

In an example embodiment, the pattern may be formed on a part or all of the surface of the prosthesis. For example, the pattern may be formed in an area corresponding to one-half or more, two-thirds or more, or three-quarters or more of the entire surface of the prosthesis.

In an example embodiment, the prosthesis may be formed of silicone.

In an example embodiment, the prosthesis may be a breast prosthesis.

In an example embodiment, the prosthesis may be for inhibiting capsular contracture.

In an example embodiment, the prosthesis may be for inhibiting an inflammatory response.

In another aspect, a technology disclosed herein provides a method of manufacturing an artificial prosthesis, the method including forming a pattern on the surface thereof, the pattern having a straight shape and being aligned in parallel.

In an example embodiment, the method may include: manufacturing a substrate having a straight and parallel aligned pattern; and injecting silicone into the substrate and hardening the silicone.

In an example embodiment, the pattern may be formed by alternate repeated parallel alignment of straight embossed portions and engraved portions.

In an example embodiment, the embossed portions may be aligned at intervals of 5 to 35 μm, and/or the engraved portions may be aligned at intervals of 5 to 35 μm.

In an example embodiment, the width of the embossed portions and the width of the engraved portion may have the same length, or the width of the embossed portions may be greater than the width of the engraved portions.

In an example embodiment, the width of the embossed portions may be greater than the width of the engraved portions by 1 to 5 μm.

In an example embodiment, a height difference between the highest point of the embossed portions and the lowest point of the engraved portions may be 0.01 to 1.5 mm.

Hereinafter, the present disclosure will be described in more detail via examples. These examples are merely illustrative of the present invention, and it will be apparent to those skilled in the art that the scope of the invention should not be construed as limited by these examples.

EXAMPLES

Patterned Substrate Design

Si substrates were designed as follows to produce a silicon prosthesis patterned at intervals of about 10 μm, 20 μm, or 30 μm.

Two wafers were used in this example. One Si wafer was designed as a control group, with a smooth surface without patterning, and the other as Si wafer for a pattern mask with an array of three patterns, which specifically were designed to have an alignment pattern at intervals of about 10 μm, 20 μm, and 30 μm. The 10 μm one was formed in twenty-six 2×2 cm square structures, and the remaining each 20 μm one and 30 μm one was formed in thirteen 2×2 cm square structures (see FIG. 1).

Patterned Substrate Production

For the production of a patterned Si substrate, a single crystal wafers was used (100 mm diameter, P/B doping, 1-0-0, and 525±25 mm thickness; Silicon Quest International). After cleaning, the wafer was immersed in buffered hydrofluoric acid, rinsed with DI, dried with $N_2$, de-watered and sintered. A barrier layer of $SiO_2$ was formed after wafer cleaning. The wafer was then primed with hexamethyldisilazane (HMDS), and a photoresist (PR) was spincoated (AZ nLOF 5510, Clariant). After lithographic patterning using projection lithography (GCA Autostep 200 i-line Wafer Stepper, 3C Technical), $O_2$ plasma processing (PE-IIA, Technics) was performed to completely remove PR residues that may remain after development. A PR pattern was then transferred to the underlying Si substrate by fluorine-based dry etching (Plasmatherm SLR 770, Uniaxis). Such a patterned Si substrate was prepared for the following two purposes: 1) a substrate with a lattice depth of 1.3 mm was used in a cell experiment; and 2) a substrate having a lattice depth of 0.3 mm was used as an imprint master in the production of a patterned Si substrate. In the latter, perfluorodecyltrichlorosilane (FDTS) coating was applied by molecular vapor deposition (MVD 100E, Applied Microstructures) to minimize resist adhesion during imprinting.

Silicone Prosthesis Sample Production

The patterned substrate produced above was used to produce a silicon prosthesis sample including a surface that has patterns formed at intervals of about 10 μm, 20 μm, and 30 μm and has a height difference of about 0.01 to 0.1 mm between embossed portions and engraved portions of the patterns. The produced silicon prosthesis with patterns formed at intervals of about 10 μm has a width of 10±2 μm between the embossed portions and a width of 8±2 μm between the engraved portions. Furthermore, the produced silicon prosthesis with patterns formed at intervals of about 20 μm has a width of 20±2 μm between the embossed portions and a width of 17±2 μm between the engraved portions. Furthermore, the produced silicon prosthesis with patterns formed at intervals of about 30 μm has a width of 30±2 μm between the embossed portions and a width of 27±2 μm between the engraved portions.

For polydimethylsiloxane (PDMS) sample production, firstly a SYLGARD™ 184 silicone elastomer base and a SYLGARD™ 184 silicon elastomer curing agent were mixed at a weight ratio of 10:1 and stirred. In order to remove bubbles generated during sample mixing, bubbles were removed by storing in a vacuum chamber for 1 hour. Silicone was then injected into the designed Si substrate fixed on a jig, spread uniformly, and cured in an oven at 60° C. for 2 hours. When the curing was complete, the jig was carefully removed so that the silicone does not tear. Once the silicone was removed, a silicone sample was produced in a desired size by using a punch.

Experimental Methods.

MTT Assay

After seeding RAW 264.7 cells on micro-patterned polydimethylsiloxane (PDMS) or control group polydimethylsiloxane (PDMS) for 24 hours, a medium was carefully removed and cells were cleaned once with PBS. MTT was added to each well at a final concentration of 0.5 mg/mL in a DMEM medium, and the cells were then cultured at 37° C. for 4 hours. An MTT solution was carefully removed, and finally formazan crystals were dissolved in DMSO. Then, absorbance was measured at 560 nm with a microplate reader (EPOCH2, BioTek).

In Vivo Implantation

For in vivo experiments, 250-300 g of 8-week-old Sprague-Dawley rats were used. Animal experimental planning has been approved by the Institutional Animal Care & Use Committee of Seoul National University Hospital (approval number: BA1803-244/030-01). In order to test in vivo responses to samples, four animals were randomly assigned to each test group (control group, 10 μm, 20 μm, and 30 μm patterns), and statistical significance thereof was obtained. The total number of animals used was 32, and animals were stored in a specific pathogen-free environment that had a 12/12 hour day/night cycle during an experiment and enabled free consumption of food and water.

An implantation surgery was performed as follows. The mice were first anesthetized with isoflurane (Hana Pharm, Seoul, Korea) during respiratory anesthesia, and all surgical tools were sterilized before the surgery. A surgical site was the center of the back site, and the animal hairs were removed with an animal clipper prior to the surgery. A 2 cm incision was made with IRIS scissors, and a pocket was secured at the center of the back site. A sterilized prosthesis was inserted by 15 cm dressing forceps, and the surgical site was sutured with nylon 4/0 (Ethicon, Somerville, N.J., USA). After the surgery, the surgical site was disinfected with Betadine. A biopsy was then performed at a given time (1st week and 8th week), and the animals were euthanized randomly in a carbon dioxide chamber. Biopsy tissue, including epidermis, dermis, capsule, and a prosthesis, was fixed with 4% paraformaldehyde and embedded in a paraffin block.

In Vivo Evaluation

A paraffin block of biopsy tissue were cut into 4 μm thick slides. The slides were immersed in xylene, 100%, 95%, 90%, 85%, and 70% (v/v) ethanol solutions for 5 minutes for rehydration and deparaffinization. Hematoxilin and eosin (H&E) staining was performed for capsule thickness analyses and inflammation analyses, and Masson's trichrome (MT) staining was performed to analyze collagen density.

A capsule thickness was determined by analyzing H&E stained tissue slides at 50× magnification by using a microscope (LSM 700, Carl Zeiss, Oberkochen, Germany). A thick collagen layer of a surface area in contact with the silicone surface was defined as a capsule. In order to evaluate the total thicknesses of the capsules of the tissue slides, three positions of capsules were imaged randomly, and a capsule thickness was measured by using ZEN software.

For IF staining, the deparaffinized slides were immersed in a 1× antigen removal (AR) solution, and microwaves were processed for 10 minutes. After 30 minutes of cooling at room temperature, the slides were cleaned three times with PBS for 5 minutes. Chlorine serum blocking solutions were applied to the slides to prevent non-specific antigen binding. Each diluted primary antibody was then reacted overnight in a dark and humid chamber. The dilution ratio of each antibody was as follows: anti-α-SMA was diluted at 1:100, and a secondary antibody was diluted at 1:2000. After secondary antibody staining, DAPI staining and mounting were performed simultaneously by using VECTASHIELD Mounting Medium (H-1200, Vector Laboratories, Burlingame, Calif., USA) equipped with DAPI. Each image was imaged at 400× magnification in a capsule site in contact with the prosthesis, and each cell was counted and analyzed by image J software.

Experimental Results.

Polydimethylsiloxane (PDMS) Patterning

Figure 2:
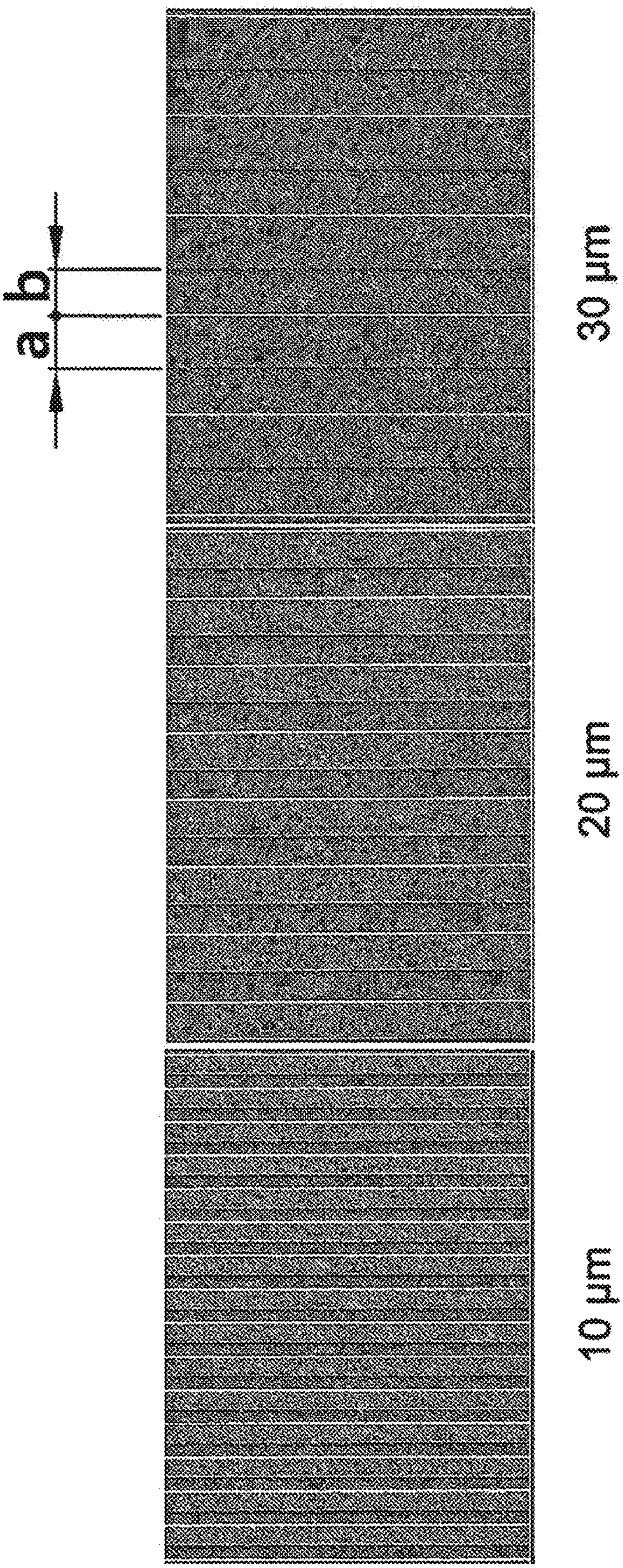
FIG. 2 illustrates a micropatterned polydimethylsiloxane (PDMS) image produced according to an example of the present disclosure.

As shown in FIG. 2, micropatterned polydimethylsiloxane (PDMS) was produced by using a stamp having embossed portions of about 10 μm, 20 μm, and 30 μm wide. As a result of SEM identification, it has been confirmed that alignment patterns with desired intervals and depths were well formed.

Macrophage Proliferation Forms

Each of RAW264.7 cells was seeded at $1\times10^5$ per well on polydimethylsiloxane (PDMS) with a smooth surface and polydimethylsiloxane (PDMS) with a patterned surface, and incubated at 37° C. After 24 hours, it was observed how fine patterning of polydimethylsiloxane (PDMS) affects macrophage morphology. As a result, it has been confirmed that the proliferative forms of macrophages differ depending on the surface shape of polydimethylsiloxane (PDMS).

Figure 3:
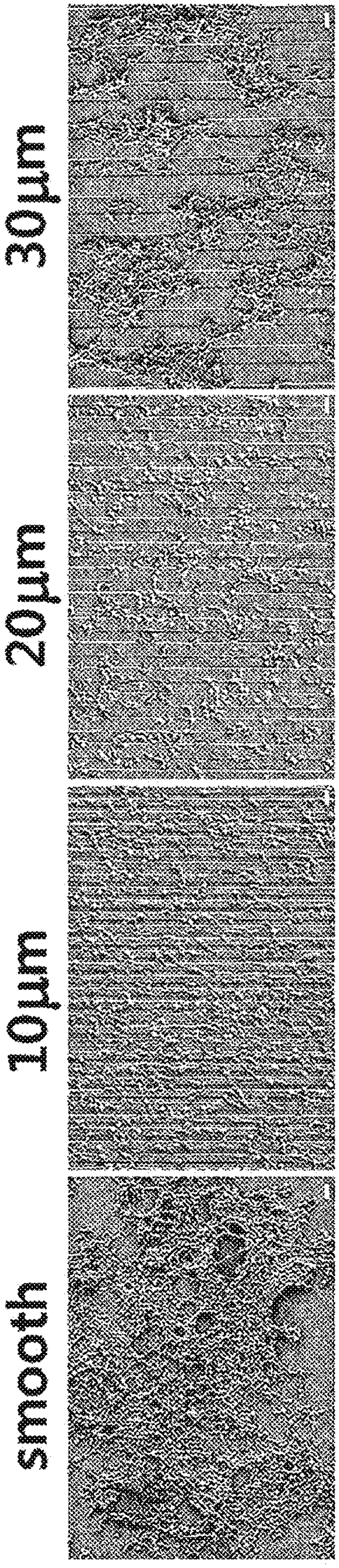
FIG. 3 shows scanning electron microscope (SEM) images confirming the effect of micropatterning of polydimethylsiloxane (PDMS) on macrophage morphology regulation in an experimental example of the present disclosure (scale bar; 20 μm).

As shown in FIG. 3, although macrophage proliferation and aggregation phenomena have been shown to be large when polydimethylsiloxane (PDMS) has a smooth surface, it has been confirmed that polydimethylsiloxane (PDMS) patterned at regular intervals and depths may inhibit these macrophage proliferation or aggregation phenomena and inhibit excessive inflammatory responses. This effect has been shown to be excellent in polydimethylsiloxane (PDMS) micropatterned especially at about 10 μm and 20 μm intervals.

Figure 4:
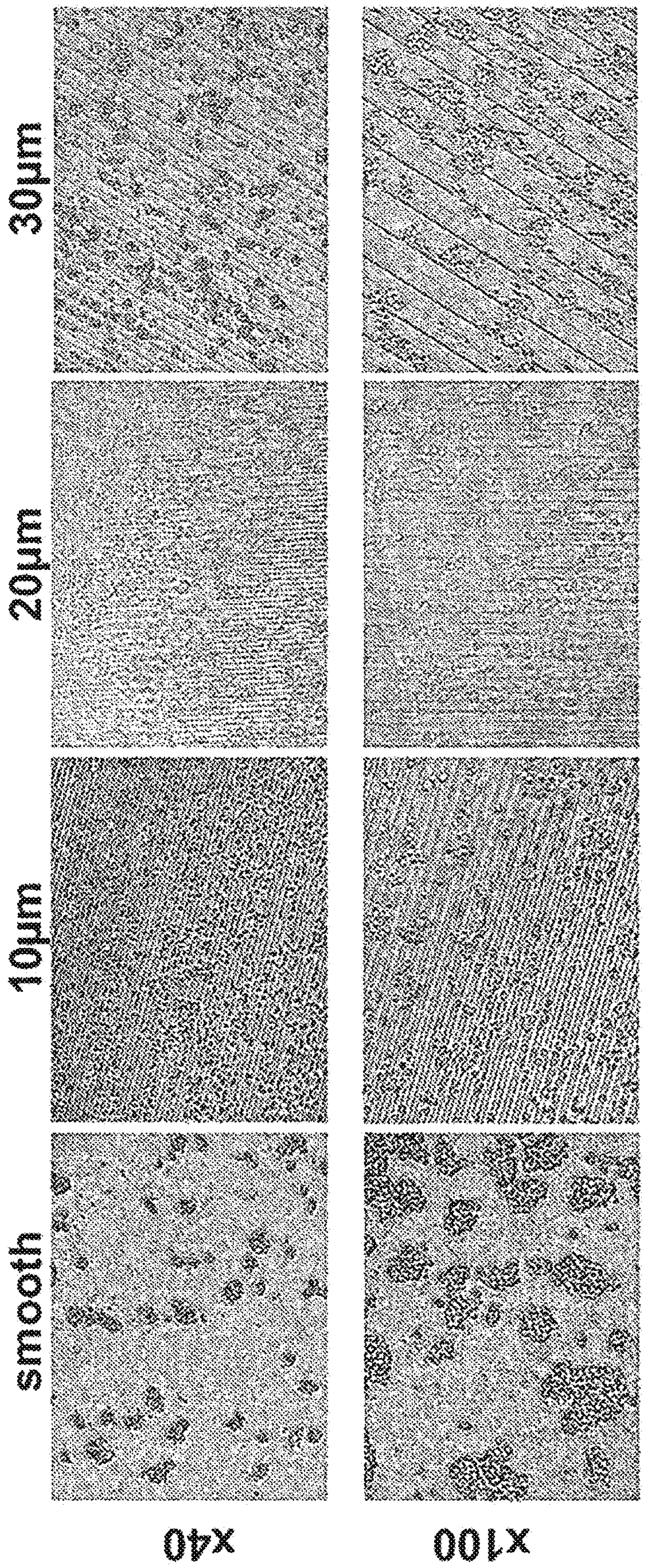
FIG. 4 is an optical microscope (O.M) image confirming the effect of micropatterning of polydimethylsiloxane (PDMS) on macrophage morphology regulation in an experimental example of the present disclosure.

Likewise, as shown in FIG. 4, RAW264.7 cells tend to be aggregated together on a conventional cell culture plate or smooth surface polydimethylsiloxane (PDMS) without a pattern to form islands between the cells, but it has been confirmed that this phenomenon is suppressed on patterned surface polydimethylsiloxane (PDMS). More cells were dispersed and elongated not to have a spherical shape in micropatterned polydimethylsiloxane (PDMS) at about 10 μm and 20 μm intervals. However, when pattern intervals became larger and larger, it has been confirmed that this phenomenon decreased and macrophages proliferated as in polydimethylsiloxane (PDMS) on a smooth surface.

Cell Viability

Figure 5:
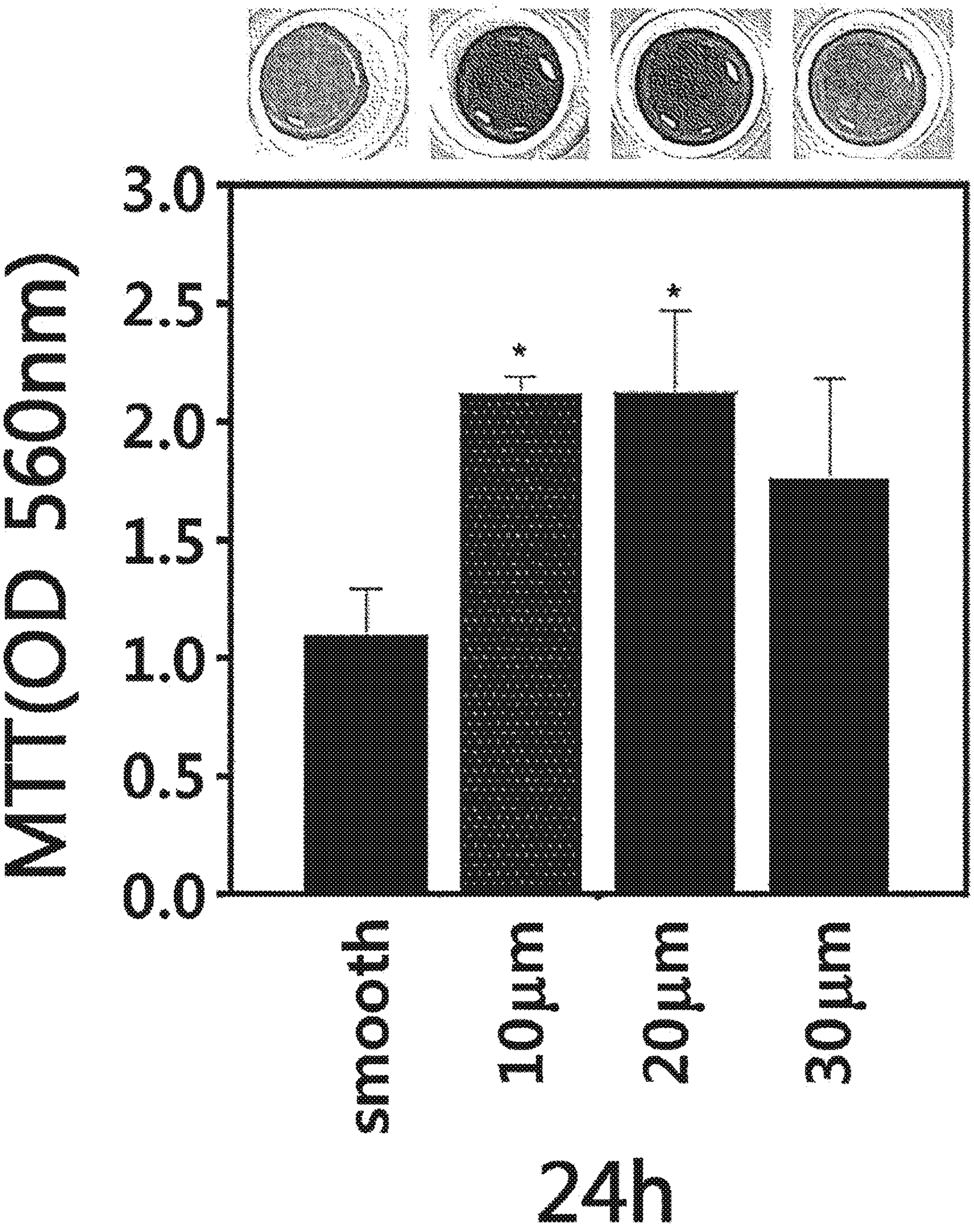
FIG. 5 shows a result of MTT assay according to an experimental example of the present disclosure (10 μm; $P<0.001$, 20 μm; $P<0.01$).

As a result of confirming by the MTT assay how the micro-patterning of polydimethylsiloxane (PDMS) affects cell viability, as shown in FIG. 5, an experimental group having polydimethylsiloxane (PDMS) with a patterned surface had averagely a higher O.D value compared to polydimethylsiloxane (PDMS) with a smooth surface. In particular, differences in cell viability were statistically significant in the polydimethylsiloxane (PDMS) experiment groups micropatterned at intervals of about 10 μm and 20 μm.

In Vivo Capsule Thickness

Figure 6A:
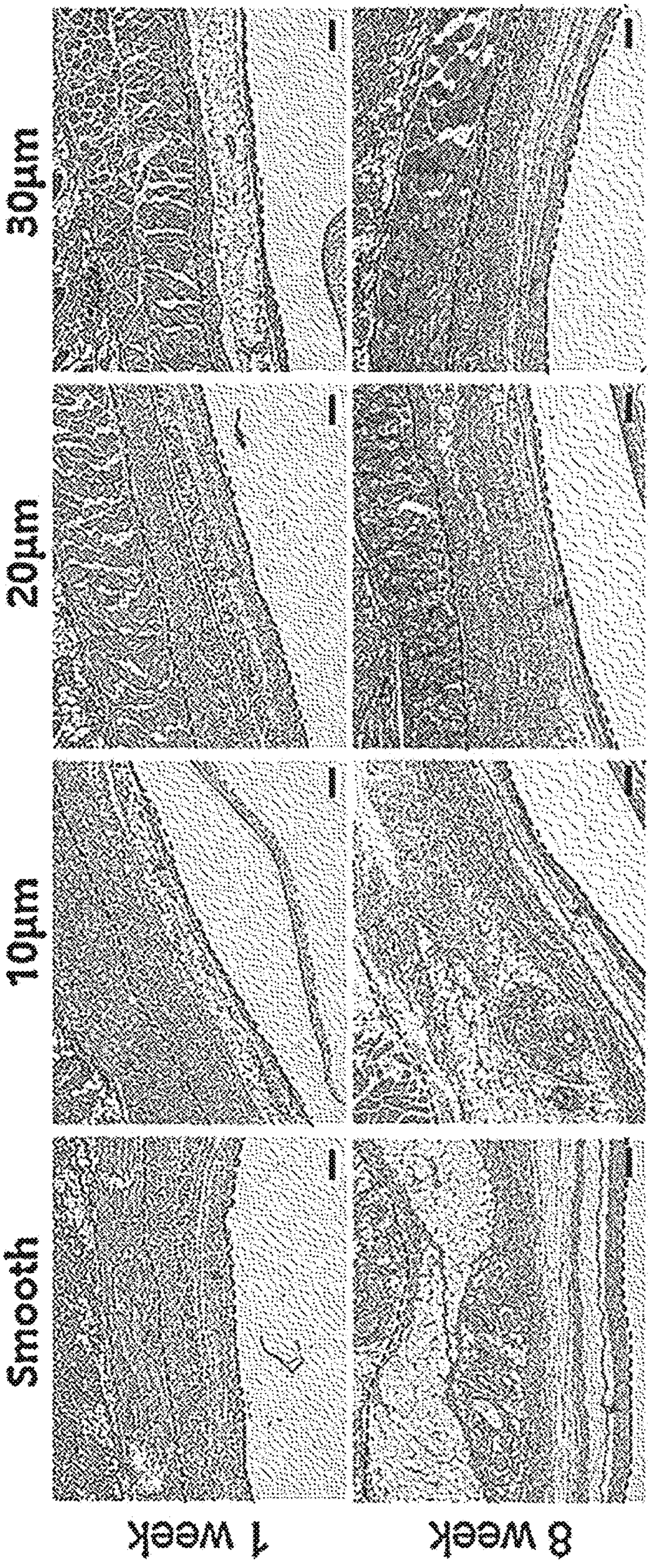
FIG. 6A shows a capsule thickness profile around a silicone prosthesis observed according to an experimental example of the present disclosure (scale bar; 200 μm). The black dotted line indicates the total thicknesses of capsules, and the blue arrow indicates the position of the silicone prosthesis and indicates a hard capsule formed on a portion contacting the silicon prosthesis.
Figure 6B:
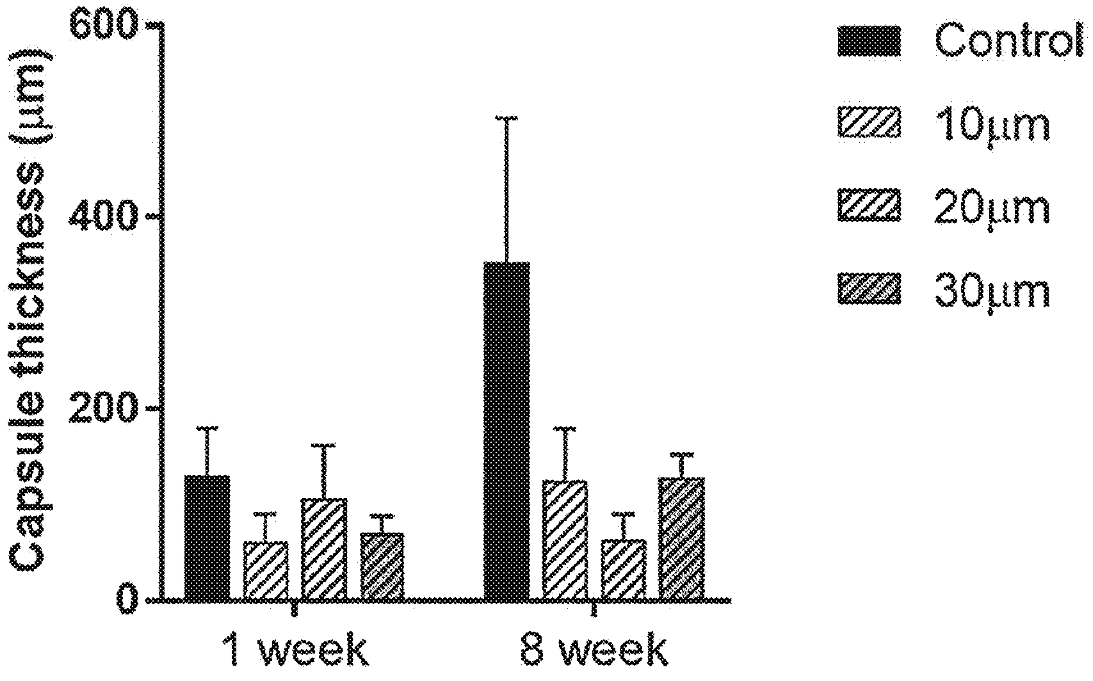
FIG. 6B compares capsule thicknesses obtained after 1 week and 8 weeks of insertion of a silicon prosthesis according to an experimental example of the present disclosure.

The results of performing implantation experiments to observe an influence of micropatterned polydimethylsiloxane (PDMS) on in vivo fibrosis inhibition are shown in FIGS. 6*a* and 6*b*.

In general, when the degree of foreign body response deteriorates, collagen formation also occurs strongly and a thick capsule is exhibited. In this experimental example, two capsule thickness analyses were performed on the polydimethylsiloxane (PDMS) upper end at the lower end of a muscle layer, and a dense capsule portion in contact with polydimethylsiloxane (PDMS). There was no significant difference in the capsule thickness between groups in week 1. However, in week 8, prostheses patterned at intervals of about 10, 20, and 30 μm had significantly reduced thicknesses of capsules in contact with surfaces compared to prostheses with smooth surfaces. In addition, when the total thicknesses of the capsules were compared, capsule thicknesses were further reduced in prostheses patterned at intervals of about 20 and 30 μm compared to a prosthesis patterned at intervals of about 10 μm. When the thicknesses of hard and dense capsules formed at portions in contact with silicone prostheses were compared to each other, a prosthesis patterned at intervals of about 20 μm exhibited the best effect of preventing capsular contracture.

Fibrosis Factor

When fibrosis is accelerated, fibroblasts differentiate into myofibroblasts, and the ability to synthesize collagen becomes stronger. Also, α-SMA is expressed. Thus, capsules may further contracted, and prostheses may be transformed. Also, pain may be caused to a patient. α-SMA is one of the most important factors for determining the degree of fiberization.

Figure 7:
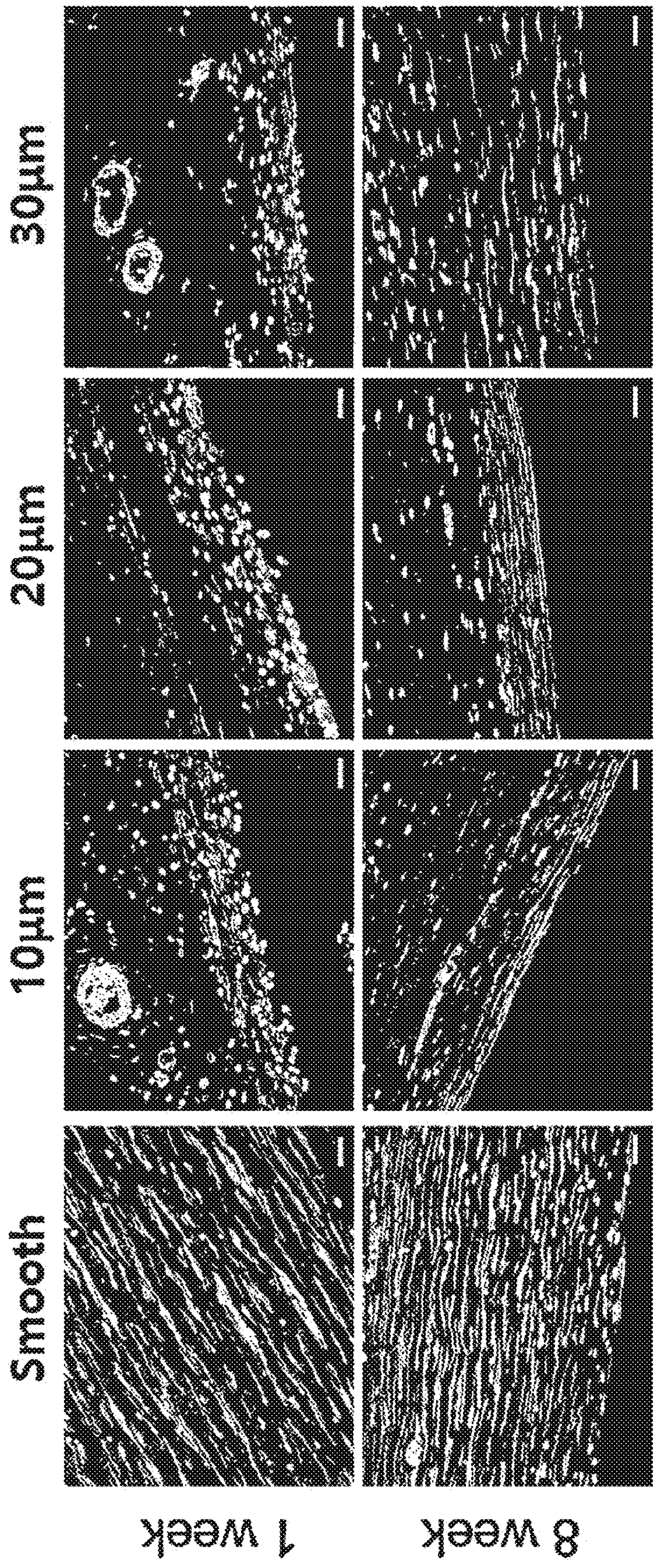
FIG. 7 shows representative histological images observed after 1 week and 8 weeks of prosthesis insertion according to an experimental experiment herein (scale bar; 20 μm).

As shown in FIG. 7, in an experimental group having a smooth surface, it has been confirmed that a thick layer was formed in a portion where α-SMA contacted a prosthesis. In an experimental group having a patterned prosthesis, α-SMA expression was reduced, and low values were observed when comparing the thickness and number of myofibroblasts. With respect thereto, a gradual increase was shown in a prosthesis patterned at about 30 μm.

While specific parts of the present disclosure have been described in detail above, it will be apparent to those skilled in the art that the specific description is merely a preferred example, and the scope of the invention is not limited thereto. It is therefore intended that the substantial scope of the invention be defined by the appended claims and their equivalents.

INDUSTRIAL APPLICABILITY

The present disclosure provides an artificial prosthesis that is usable for breast molding, reconstruction, and the like, and a method for manufacturing the same. The artificial prosthesis may reduce inflammation at an implantation site and effectively reduce capsular contracture side effects.

The invention claimed is:

1. An artificial prosthesis comprising a surface having a pattern formed thereon, wherein the pattern comprises straight line shapes aligned in parallel, and wherein the pattern is formed by alternate repeated parallel alignment of straight embossed portions and engraved portions, the embossed portions are aligned at a width of 15 to 25 μm and the engraved portions are aligned at a width of 10 to 25 μm, and the height difference between the highest point of the embossed portions and the lowest point of the engraved portions is 0.01 to 1.0 mm.

2. The artificial prosthesis according to claim 1, wherein the embossed portions are aligned at a width of 18 to 22 μm, and/or the engraved portions are aligned at a width of 15 to 20 μm.

3. The artificial prosthesis according to claim 1, wherein the width of the embossed portions and the width of the engraved portion have the same length, or the width of the embossed portions is greater than the width of the engraved portions.

4. The artificial prosthesis according to claim 1, wherein the width of the embossed portions is greater than the width of the engraved portions by 1 to 5 μm.

5. The artificial prosthesis according to claim 1, wherein the height difference between the highest point of the embossed portions and the lowest point of the engraved portions is 0.01 to 0.1 mm.

6. The artificial prosthesis according to claim 1, wherein the prosthesis is formed of silicone.

7. The artificial prosthesis according to claim 1, wherein the prosthesis is a breast prosthesis.

8. The artificial prosthesis according to claim 1, wherein the prosthesis is for inhibiting capsular contracture.

9. The artificial prosthesis according to claim 1, wherein the prosthesis is for inhibiting an inflammatory response.

* * * * *